United States Patent [19]

Walele et al.

[11] Patent Number: 5,270,461

[45] Date of Patent: Dec. 14, 1993

[54] BENZOATE ESTERS OF ALKOXYLATED METHYL GLUCOSIDES

[75] Inventors: Ismail I. Walele, Saddle Brook, N.J.; Nicholas J. Scarangella, West Nyack, N.Y.; Anthony Ansaldi, Stanhope; Ann M. Andrews, Saddle Brook; Samad A. Syed, Jersey City, all of N.J.

[73] Assignee: Finetex, Inc., Elmwood Park, N.J.

[21] Appl. No.: 795,868

[22] Filed: Nov. 19, 1991

[51] Int. Cl.⁵ .................. C07H 13/02; C07H 15/04
[52] U.S. Cl. ................................. 536/116; 536/119; 536/120
[58] Field of Search ............... 536/119, 120, 116, 4.1; 549/417; 424/59, 68, 70; 514/458, 844, 969

[56] References Cited

U.S. PATENT DOCUMENTS

| | | | |
|---|---|---|---|
| 4,323,694 | 4/1982 | Scala | 560/103 |
| 4,791,097 | 12/1988 | Walele et al. | 560/112 |
| 5,059,443 | 10/1991 | Ennis et al. | 536/18.3 |

OTHER PUBLICATIONS

Chemical Abstracts, vol. 79, No. 21, issued Nov. 26, 1973, Deferrari et al, "NMR Spectra of some Sugar Perbenzoates" see p. 431, column 1, abstract No. 126720j, *An. Asoc. Quim. Argent*, 1973, 61(3), 107–12 (Eng).

Chemical Abstract, vol. 86, No. 1, issued Jan. 3, 1977, Lundt et al, "Preparation of 2-deoxy Sugars by Hydrogenolysis of Benzoylated Glycopyranosyl Bromies. Part II." see p. 497, column 2, abstract No. 5705u, *Acta Chem. Scand. Ser. B* 1976, B 30(7), 680–4 (Eng).

Chemical Abstract, vol. 101, No. 10, issued Sep. 3, 1984, Guidini et al, "Processing of Whey. III. Synthesis of Lactose and Lactitol Benzoates" see p. 108, column, abstract No. 74677b, *Lait* 1983, 63 (633–634), 463–72 (Fr).

Chemical Abstract, vol. 107, No. 21, issued Nov. 23, 1987, Tietze et al, "Glycosidation. VII. Development of Selective Cytostatica for Cancer Therapy. Synthesis of acetal-$\beta$-glucosides from Cytotoxic Aldehydes" see p. 808, column 2, abstract No. 198790b, *Liebigs Ann. chem.* 1987, (10), 847–56 (Eng).

Chemical Abstracts, vol. 112, No. 5, issued Jan. 29, 1990, Uzawa et al, "Application of the Dibenzoate Chirality Method to Determine the Abosolute Configuration of Glycerols and Related Acyclic Alcohols" see p. 628, column 1, abstract No. 36314a, *J. Org. Chem.* 1990, 55(1), 116–22 (Eng).

*Primary Examiner*—Johnnie R. Brown
*Assistant Examiner*—Everett White
*Attorney, Agent, or Firm*—Weingram & Zall

[57] ABSTRACT

Benzoic acid esters of an ethoxylated methyl glucosides and of a propoxylated methyl glucosides exhibit enhanced characteristics that make these esters ideally suited for skin and hair care compositions. These esters demonstrate enhanced capabilities as foam boosters, emollients, conditioners, clarifiers, solubilizers, and carriers (diluents). In addition, oxybenzone, benzocaine, ibuprofin and dihydroxyacetone (DHA) can be solubilized by these esters. These esters have the ability to solubilize both hydrophilic and hydrophobic materials such as DHA. The benzoate esters have lower surface tensions than the glucam polyol molecules from which they were derived.

2 Claims, No Drawings

BENZOATE ESTERS OF ALKOXYLATED METHYL GLUCOSIDES

BACKGROUND OF THE INVENTION

1. Field of the Invention

This invention relates generally to improved ester compositions, and more particularly to certain benzoate esters of ethoxylated and propoxylated methyl glucosides which are useful as foam modifiers, emollients, conditioners, and clarifiers.

2. Description of the Prior Art

Numerous references describe the production and use of benzoic acid esters. None of these references teach or suggest the specific novel benzoate esters of this invention or the use of these benzoate esters as foam modifiers, clarity enhancers, emulsification enhancers, or conditioners for hair shampoo and hair conditioners. More specifically:

U.S. Pat. No. 3,714,228 to Massie describes the reaction of benzoic acid with benzyl alcohol in the presence of a catalyst to produce benzyl benzoate. Other compounds produced are benzyl acetate, benzyl propionate, etc.

U.S. Pat. No. 3,758,547 to Robin, et al., describes a process for reacting benzoic acid with an amino alcohol using certain catalysts.

U.S. Pat. No. 3,916,008 to Green, et al., describes a class of esters which are useful for the control of serum cholesterol levels in animals and man. One group of esters included within the invention include the esters of the surfactants sold under the trade name "Tetronic 701" and "Tetronic 702". Reference is made to formula II, wherein the groups $R_1$, $R_2$, $R_3$, and $R_4$ include benzyl and substituted benzyl.

U.S. Pat. No. 3,929,848 to Snapp Jr., et al., describes a series of ether-diester derivatives of p-dioxanone having a formula:

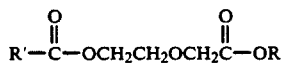

wherein R' is an alkyl of from 1 to 7 carbon atoms or the phenyl moiety and R is an alkyl of from 1 to 8 carbon atoms.

U.S. Pat. No. 4,243,799 to Mueller, et al., describes a process for the preparation of polybutylene glycol carboxylic acid diesters.

U.S. Pat. Nos. 4,275,222 and 4,322,545 to Scala, Jr. describes benzoic acid esters of linear primary alcohols and their use as diluents, solvents and platicizers, and liquid carriers.

U.S. Pat. No. 4,323,694 to Scala, Jr., describes benzoic acid esters of linear and branched alcohols and their use in toiletry and cosmetic formulations.

U.S. Pat. No. 4,323,693 to Scala, Jr., describes benzoic acid esters of isostearyl ($C_{18}$) alcohol and their use in toiletry and cosmetic formulations.

U.S. Pat. No. 4,359,478 to Schomolka describes certain polyoxybutylene-polyoxyethylene block copolymers and their mono or diesters for use in a diet as a hypocholesterolaemic agent. The diesters are of the formula:

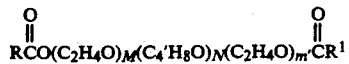

wherein R and $R^1$ are H or aryl or aliphatic with suitable esters being benzoate esters.

U.S. Pat. No. 4,431,837 to Geria describes long chain aliphatic hydrocarbon ethoxylated alcohol benzoates having a small degree of ethoxylation and believed to be of the general formula:

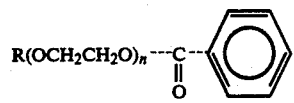

in which R is a long chain aliphatic hydrocarbon radical having from about 8 to about 18 carbon atoms and n is a number no greater than about 5. These benzoates are useful as vehicles in pharmaceutical, cosmetic and toiletry preparations.

U.S. Pat. No. 4,528,106 to Grolitzer describes nonionic polyalkoxylated glucoside surfactant compositions. This reference describes Glucam E and Glucam P, in particular,

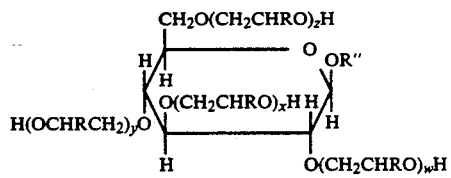

wherein each R is individually selected from the group consisting of a hydrogen and a methyl group; wherein the sum of $w+x+y+z$ is from about 4 to 40; R" is a lower alkyl group having 1 to 4 carbon atoms with a polyalkoxylated alcohol of the formula:

wherein m is from about 2 to about 15; and wherein R' is selected from the group consisting of an alkyl group having about 6 to about 20 carbon atoms, an alkenyl group having about 6 to about 20 carbon atoms and an alkyl aryl group having about 10 to about 20 carbon atoms. This reference uses Glucam as a starting material to produce a polyalkoxylated glucoside.

U.S. Pat. No. 4,791,097 to Walele. et al., describes benzoate esters used as foam enhancers. The benzoate ester is of the formula:

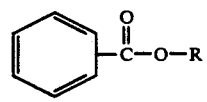

wherein R is:

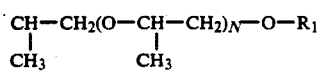

wherein n is 9–16 and $R_1$ is a branched or linear alkyl of 3 to 22 carbon atoms, or of the formula:

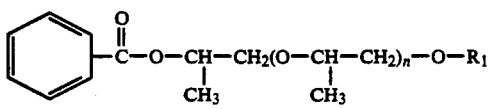

wherein n is 9 to 16 and $R_1$ is a branched or linear alkyl of 3 to 22 carbon atoms.

U.S. Pat. No. 4,323,694 to Scala, Jr. describes benzoic acid esters of alcohols.

SUMMARY OF THE INVENTION

An object of this invention is to provide improved benzoic acid ester compositions.

A further object of this invention is to provide novel benzoic acid esters which may serve as foam boosters, emollients, conditioners, clarifiers, solubilizers, and carriers or diluents.

A still further object of this invention is to provide benzoate esters of glucam E and glucam P alkoxylated methyl glucoside polyols.

Another object of this invention is to provide esters that enhance the clarity and foam boosting characteristics of hair care products such as shampoos and conditioners.

Still another object of this invention is to provide esters that enhance the wet comb, dry comb, and flyaway characteristics of hair care products.

A further object of this invention is to provide esters with enhanced abilities to solubilize oxybenzone, benzocaine, ibuprofin and dihydroxyacetone (DHA).

A still further object of their invention is to provide esters with the ability to solubilize both hydrophilic and hydrophobic materials such as DHA.

Another object of this invention is to provide esters with an improved affinity for water/propylene glycol/glycerin while maintaining clarity.

Still another object of this invention is to provide esters with lower surface tensions so that when incorporated into skin care and cosmetic compositions, the product has a better distribution on the skin, a more uniform film results and film thickness is better controlled.

A still further object of this invention is to provide esters which will enhance the look and feel characteristics of skin and hair care products such as soaps, tanning lotions, dry-skin lotions, urban protection creams, hydrophilic ointments, hand, face or body lotions with vitamins and antiperspirants.

All of the foregoing objects are achieved by benzoic acid esters of ethoxylated methyl glucosides based on modified glucam E molecules (commercially available from Amerchol Corp.) and benzoic acid esters of propoxylated methyl glucosides based on modified glucam P molecules (commercially available from Amerchol Corp).

DETAILED DESCRIPTION OF THE INVENTION

The benzoic acid esters of this invention are produced by reacting benzoic acid with an ethoxylated or propoxylated methyl glucosides. Preferably, stannous oxalate is used as a catalyst. It is contemplated, however, that any method of producing such benzoic acid esters can be utilized as long as such method does not interfere with the intended use of the esters. In particular, the process for producing the esters should permit them to be purified to a substantially pure condition. By the use of the term "substantially pure", it is meant that the compositions do not contain impurities which would interfere with the intended use of the esters.

Glucam E (ethoxylates) and glucam P (propoxylates) are alkoxylated glucose derivatives that are commercially available from Amerchol Corp. Glucam derivatives are multifunctional polyols with broad solubility profiles, strong water retention properties, exceptionally light color, low odor, and soothing and conditioning properties.

The chemical structure for glucam E is:

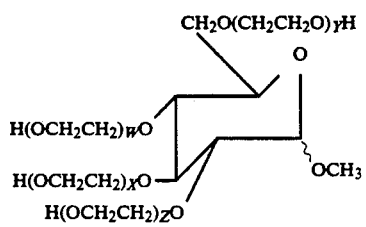

Wherein:
Glucam E-10, $W+X+Y+Z$ averages about 10
Glucam E-20, $W+X+Y+Z$ averages about 20

The chemical structure for glucam P. is:

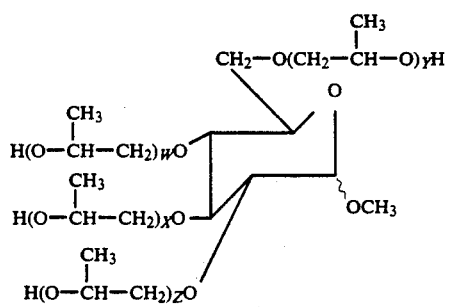

Wherein:
Glucam P-10, $W+X+Y+Z$ averages about 10
Glucam P-20, $W+X+Y+Z$ averages about 20

The benzoate esters of the present invention are produced by reacting the glucam polyols i.e. glucam E or glucam P, with benzoic acid to produce the novel esters of this invention and the esters used in this invention.

The structure of these benzoate esters is:

Benzoates of ethoxylated methyl glucosides based upon modified glucam E molecules:

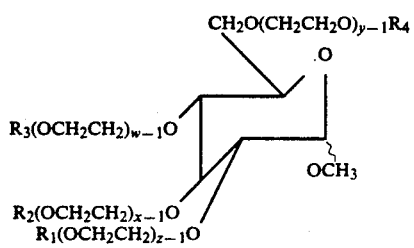

Wherein $R_1$, $R_2$, $R_3$ and $R_4$ are each independently selected from:

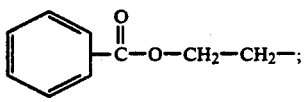

and wherein for:

Glucam E-10, W+X+Y+Z is an average of about 10 moles of ethylene oxide

Glucam E-20, W+X+Y+Z is average of about 20 moles of ethylene oxide

Benzoates of propoxylated methyl glucosides based upon modified glucam P molecules:

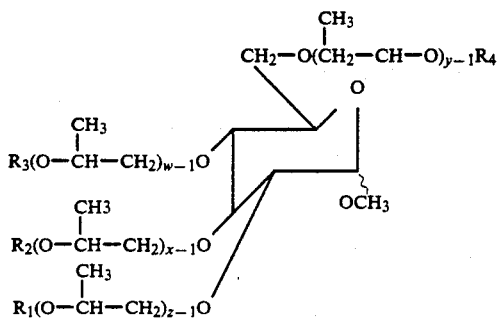

Wherein $R_1$, $R_2$, $R_3$ or $R_4$ are each:

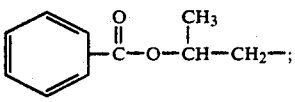

and wherein for:

Glucam P-10, W+X+Y+Z is an average of about 10 moles of propylene oxide

Glucam P-20, W+X+Y+Z is an average of about 20 moles of propylene oxide

The compositions of this invention are useful as:
Emollients—solubilizers
Moisturizers—plasticizers
Sunscreen vehicles/solvents
Hair conditioners/detanglers
Wetting agents for powders
De-oilers/degreasers
Emulsifiers/co-emulsifiers
Viscosity-modifiers
Foam-modifiers
Facial cleansers The foregoing list is only exemplary of the type of compositions in which the benzoic acid esters of this invention may be used and, as such, is not to be considered limiting.

The amount of ester used in aqueous surfactant composition is dependent on the type of composition desired, the type and quantity of other ingredients used, e.g. cosmetic ingredients, and the amount and type of functional additives that are utilized. Typically, the amount of ranges from about 0.5% to about 50% by weight of the aqueous surfactant composition. Preferably, from about 0.5% to about 5.0% of benzoic acid esters of this invention are used.

The aforedescribed benzoic acid esters have unique properties. In particular, they have foam modifying properties. By "foam modification" herein it is meant that the benzoic acid esters confer any or all of the following properties upon a surfactant composition:
Flash foam increase;
Flash volume increase;
Foam viscosity increase or decrease;
Foam cell size increase or decrease.

While the particular foam modification is dependent upon the benzoic acid ester and surfactant of choice, no surfactant investigated has been observed to suffer a suppression of foam volume due to the presence of any of the benzoic acid esters investigated herein, i.e. none of the benzoic acid esters investigated were defoamers. Additionally, they have other properties which make them suitable for use as emollient carriers and for use as solvents.

Further, they possess other unusual physico-chemical properties, in particular, high spreading coefficients, which can make them beneficial and unique components of sophisticated delivery systems—such as in hand, face, and body creams and lotions.

The benzoate esters of this invention may be used in skin care compositions. The amount used in skin care compositions is dependent on the type of skin care compositions, the type and quantity of cosmetic ingredients used and the amount and type of functional additives. Typically the amount ranges from about 0.5% to about 80%, by weight, of the skin care compositions. For example, a facial cream may only have about 0.5%, where a massage oil may have up to about 80% by weight. Still higher amounts may be used in, for example bath oils, e.g. 95%.

Further, the benzoate esters described herein are solvents and/or vehicles for ultraviolet (UV) absorbers. Such esters may also function as plasticizers for polymers contained in skin care compositions, may be auxiliary suspending agents capable of assisting in the suspension of ingredients in skin care compositions and also may function as a dye leveling agent and dye carrier. Thus, the benzoate ester when used in skin care compositions serves not only as an emollient and carrier but also exhibits one or more other functions.

The aforedescribed benzoic acid esters have the following properties:
1. Water solubility/dispersibility
2. Ease of emulsification
3. Emulsifier/co-emulsifier with other emollients
4. Emolliency at body temperature with good afterfeel
5. Lack of greasiness, pleasant skin feel.
6. Lack of oiliness while imparting good lubrication.
7. Viscosity improvements without extraneous thickeners
8. Foam improvements with viscosity increases
9. Low cloud points and pour points.
10. Unusually high spreading coefficient.
11. Gel formation—ability to form gels with suspending agents;
12. Bland odor;
13. Alcohol (ethanol) solubility
14. Dispersibility in propylene glycol/glycerine/water
15. Allows more water in some systems
16. Pearlescence in emulsions without pearlescing agents
17. Low toxicity.
18. Acid, alkaline stability.

19. Clear stable emulsions/micro emulsion at 45° C. and yet on cooling becomes an emulsion/cream
20. Solvents for many uncommon skin and hair additives, including, sunscreens and over-the-counter therapy 'actives'.

The following are non-limiting examples of the compositions of this invention and the uses of these compositions in hair and skin care compositions wherein foam modification, clarity, emulsification, or conditioning properties are needed.

EXAMPLE 1

Preparation of Methyl Gluceth-10-Benzoate (EMG-10)

A mixture of 222 gms. of Glucam E-10 (methyl-gluceth-10 from Amerchol Corp.), 78 gms. of benzoic acid and 1 gm. of stannous oxalate was heated under nitrogen purge to 200° C. over one hour and reacted at 200°-220° C. for 2 hours. At the end of this reaction time, the acid value was 6.84 mgms. KOH/gm. The net yield was 205 gms. of crude ester in the reaction flask with a combined loss of 35 gms. of water and sublimate. The crude ester was a dark reddish, very viscous liquid.

The crude ester was washed at 80° C. with 2.5 gms. of sodium carbonate, 2.5 gms. of hydrogen peroxide, 30 gms. of sodium sulfate and 150 gms. of water. The net ester (347 gms. top layer 1 was then washed with 22 gms. of sodium sulfate and 100 gms. of water containing 1.5 gms. of acetic acid at 60° C. The yield was 343 gms. of wet ester. This wet ester was then dried at 105° C. for a yield of 180 gms. of dry refined ester.

EXAMPLE 2

Preparation of Methyl-Gluceth-10 Benzoate (EMG-10

A mixture of 650 gms. of Glucam E-10 (methyl-gluceth-10 from Amerchol Chem. Co.) and 170 mgms. of sodium borohydride was stirred for 2 hours at 50° C. To this mixture at 70° C., was added 228 gms. of benzoic acid and 1.32 gms. of stannous oxalate. The reaction was carried out as in Example 1 until the acid value reached 15.26 mgms. KOH/gm. The product was then cooled to 100° C. Then 8.5 gms. of hydrogen peroxide was added to bleach the mixture from dark brown liquid to light amber liquid.

The crude ester yield of 808 gms. was subjected to washing with 450 gms. of water containing 18 gms. of sodium carbonate, 60 gms. of sodium sulfate and 8 gms. of hydrogen peroxide at 70°-75° C. for ½ hour. An additional 8 gms. of hydrogen peroxide were used to further bleach the crude ester to a very light colored liquid. The yield was 1028 gms. of the wet ester.

A second wash was carried out at 70° C. with 250 gms. of water containing 40 gms. of sodium sulfate and 2 gms of acetic acid. Upon separation, 1100 gms. of the wet ester was collected and subjected to drying at 110° C. This mixture, being very viscous, was diluted with 100 mls. of isopropanol and treated with 0.5 gm. of CELATOM FW-60. Filtration using Whatman #4 paper gave a crystal clear liquid, which was then subjected to distillation at 80°-85° C. and a vacuum of 20-25" Hg. The resulting product was a hazy/semi-translucent liquid. To this mixture was added 50 gms. of water which then yielded a clear product.

EXAMPLE 3

Preparation of Methyl Gluceth-20-Benzoate (EMG-20)

A mixture of 249 gms. of glucam E-20 (methyl gluceth-20 from Amerchol Chem. Corp.), 51 gms. of benzoic acid and 1 gm. of stannous oxalate was heated under nitrogen purge to 200° C. for over one hour and then brought to 220° C. The reaction was continued at 220° C. for 2 hours. At the end of the 2 hours of reaction time, the acid value was 17.37 mgms. KOH/gm. The net yield in the reaction flask was 280.5 gms. of the crude ester.

The crude ester was washed at 80° C. with 5.5 gms. of sodium carbonate, 25 gms. of sodium sulfate, 5.0 gms. of hydrogen peroxide and 200 gms. of water. The wet ester (344 gms.) was then washed with 25 gm. of sodium sulfate, 1 gm. of acetic acid and 175 gms. of water at 70° C. The product layer, upon standing, was collected and weighed 374 gms. as a wet refined ester. This wet ester was dried at 100°-115° C. and a vacuum of up to 27" Hg to yield 222 gms. of refined ester as a crystal clear liquid.

EXAMPLE 4

Preparation of Methyl Gluceth-20 Benzoate (EMG-20)

A mixture of 664 gms. of glucam E-20 (methyl-gluceth-20 from Amerchol Chem. Corp.), 136 gms. of benzoic acid and 2.4 gms. of stannous oxalate was reacted at 200°-205° C. for 3 hours. At the end of this reaction period, the acid value was 4.42 mgm KOH/gm.

The mixture was cooled to 100° C. and 3.5 gm. of hydrogen peroxide was added. The bleached mixture was lighter in color. The yield was 747 gms. of ester. This ester was washed with 530 gm. of water containing 6 gms. of sodium carbonate, 70 gms. of sodium sulfate and 10 gms. of hydrogen peroxide. The resulting very viscous, heterogenous mixture was allowed to stand. The aqueous layer was removed with the top produce layer of 910 gms. as the ester was collected. This product was then subjected to washing with 350 gms. of water containing 50 gms. of sodium sulfate and 2.5 gm. acetic acid at 50° C. The wet ester collected was 1083 gms. which was dried at 105°-110° C. until 385 gms. of water was distilled off. The product showed very slight haze.

To this mixture, 20 gms. of water was added. A very slight haze was observed. CELATOM FW-60 was used to filter the product. Upon filtration a clear liquid ester was obtained. The yield was 772 gms. of refined ester.

EXAMPLE 5

Description of Reactants with Benzoic Acid

| GLUCAM REACTANT WITH BENZOIC ACID | EXAMPLE NUMBER | AVERAGE MOLECULAR WEIGHT | MOLES % EO | MOLES % PO | RANGE OF MOLECULAR WEIGHT |
| --- | --- | --- | --- | --- | --- |
| E-10 | 1,2 | 623 | 10 | | 606–641 |
| E-20 | 3,4 | 1,044 | 20 | | 997–1095 |
| P-10 | | 761 | | 10 | 736–787 |

| GLUCAM REACTANT WITH BENZOIC ACID | EXAMPLE NUMBER | AVERAGE MOLECULAR WEIGHT | MOLES % EO | MOLES % PO | RANGE OF MOLECULAR WEIGHT |
|---|---|---|---|---|---|
| P-20 | | 1,320 | | 20 | 1247–1403 |

EO is ethylene oxide
PO is propylene oxide.

EXAMPLE 6

Effect of Esters on Clarity and Forms of Clear Conditioning Shampoo

A shampoo base which is clear, mild and conditioning was prepared by charging the water and heating to 60°–20° C. The following ingredients were added in the order given, while the temperature of the shampoo base was maintained until all ingredients were fully incorporated. Preservative fragrance and color can be added, as desired. The viscosity of the shampoo base increased upon cooling.

| Component | % by Weight |
|---|---|
| Standapol A (Ammonium Lauryl Sulfate) | 15.0 |
| TAURANOL I-78-6 (Sodium Cocoyl Isethionate) | 10.0 |
| FINQUAT CT (Quaternium 75) | 5.0 |
| AMINOL HCA (Cocamide DEA) | 5.0 |
| Propylene Glycol | — |
| Water | 65.0 |

The esters of the inventions were added at a 3% level directly into the shampoo base to determine the effect on clarity and foam versus the control without the ester.

The following data illustrates that the new esters not only maintained clarity but also enhanced the foam performance. Prior art esters have traditionally been foam depressants and, in addition, have formed emulsions when placed into water systems. The data for the EMG-20 (benzoate of ethoxylated (10 EO) methylglucoside (glucam) in combination with conditioning data for EMG-20 (benzoate of ethoxylated (20 EO) methylglucoside (shown in a later example) strongly indicates the possibility of developing a clear conditioning shampoo.

EXAMPLE 7

Conditioning Effect on Hair

The method used comprised rinsing each one gram tress sample under warm water. Placing one of each tress into a formulation. Letting each tress sit in solution for five minutes. Rinsing under warm water. Hanging and performing wet comb, dry comb and flyaway.

The shampoo base formula comprised:

| Chemicals | % |
|---|---|
| A-Ammonium Lauryl Sulfate | 30.00 |
| Cocoamide Diethanolamine | 5.0 |
| Water | 41.25 |
| B-Ammonium chloride | 2.0 |
| Water | 6.0 |
| C-Water | 15.75 (Q.S.) |

This shampoo base was formulated as follows:
1. Combine phase A Chemicals
2. Heat to 55° C.
3. Combine phase B chemicals
4. When phase A chemicals are at 55° C., add phase B chemicals to phase A chemicals
5. Mix for five minutes
6. Cool and continue mixing until chemicals reach room temperature.

Note that the 15.75% water (phase C) left out of the formula will be Q.S. with each conditioner at 5.0% level and water.

| Each batch consists of | 84.25% | base |
|---|---|---|
| | 10.75% | distilled water |
| | 5.00% | ester or dimethicone |
| | 100.00 | |

The results were as follows:

| Ester | Initial | Overnight | FOAM HEIGHT* 0 min. | 5 min. |
|---|---|---|---|---|
| | APPEARANCE | | | |
| Control without ester | Clear | Clear | 293** | 293*** |
| | PRIOR ART | | | |
| TN[4] | Emulsion | Sep. | 220 | 210 |
| IPM[5] | Emulsion | Sep. | 245 | 245 |
| P.G.dicaprylate/dicaprate | Emulsion | Sep. | 200 | 200 |
| Caprylic/Capric T.G. | Emulsion | Sep. | 273** | 273** |
| NEW ESTERS BASED ON BENZOATES OF ETHOXYCATED METHYL GLUCOSIDES (GLUCAM E) | | | | |
| EMG-10-BENZOATE of Invention | Clear | Clear | 300 | 300 |
| EMG-20-BENZOATE of Invention | Clear | Clear | 340 | 340 |

[1] Sample showed slight sediments on bottom
[2] 0.5% Soln.
[3] Avg. of 2 trials
[4] $C_{12-15}$ alkyl benzoates
[5] Isopropyl Palmitate.

| Batch | Wet Comb | Dry Comb | Fly Away |
|---|---|---|---|
| Shampoo base (base) | 9 | 5 | 3 inches |
| Base with dimethicone[1] | 5 | 1 | 2 inches |
| Base with dimethicone copolyol[2] | 7 | 2.5 | 6 inches |
| Base with glucam E-10 benzoate ester | 5 | 1.5 | 4 inches |
| Base with glucam E-20 benzoate ester | 4 | 1.5 | 3 inches |

[1]Dimethicone 200 fluid - Dow Corning Corp.
[2]Dimethicone copolyol - Dow Corning Corp.

The rating scale used was 1=Best, 10=worst. The above results show that dimethicone and glucam E-10 benzoate ester are both comparable in their effect on wet hair. However, the results indicate that the glucam E-20 benzoate ester is the best ester to enhance wet comb.

The dry comb results show that the dimethicone and glucam E-10 and E-20 benzoate esters affect dry comb. The glucam E-20 benzoate ester gives the most enhanced wet comb results coupled with excellent dry comb results.

Overall, the dimethicone is the best emollient in this study. The results obtained for the glucam E-20 benzoate ester also indicate that this ester is a promising emollient.

EXAMPLE 8

Solubility of Active Compounds in the Esters of this Invention

The solubility of both the commercially available esters and the experimental esters used in these tests are as follows:

| Esters | Name | Oxybenzone | DHA | Benzocaine | Ibuprofin[1] |
|---|---|---|---|---|---|
| | | COMMERCIAL ESTERS FINESOLV | | | |
| TN | C12-15 alkyl benzoate | 22 | <1 | 4.0 | 12.0 |
| SB | Isostearyl benzoate | 17 | <1 | 3.0 | 9.0 |
| BOD | Octyl dodecyl benzoate | 16 | <1 | 1.0 | 7.0 |
| P | PPG-15 stearoxy benzoate | 21 | <1 | 11.0 | 20.0 |
| | | Esters of Invention | | | |
| EMG-10 | Methyl gluceth-10 benzoate | 19 | 17 | 27.0 | 29.0 |
| EMG-20 | Methyl gluceth-20 benzoate | 19 | 17 | 29.0 | 29.0 |

[1]Average values rounded to the nearest whole number

The above results show that the esters of this invention have several advantages over the commercial esters used in these trials. The esters of this invention demonstrated an ability to solubilize oxybenzone, an oil rebuffing material. Oxybenzone is a typical UVA absorber used in sunscreen preparations.

In addition, an exceptional improvement was observed in solubilizing benzocaine (a local anesthetic type material) and ibuprofin (a topical anti-inflammatory).

The really unexpected results are the ability of the esters EMG-10 and EMG-20 of this invention to solubilize DHA a very hydrophilic material which is not easy to solubilize. DHA is also a premier self-tanning material.

This unique ability of being able to solubilize both hydrophilic and hydrophobic materials opens up entirely new formulating possibilities. Whereas, previously, these materials had to be emulsified to be combined in the same system, the benzoate ester can now couple these types of materials together in the same system, while maintaining clarity and with the use of little or no surfactant.

The structure of the active ingredients used in these trials is as follows:

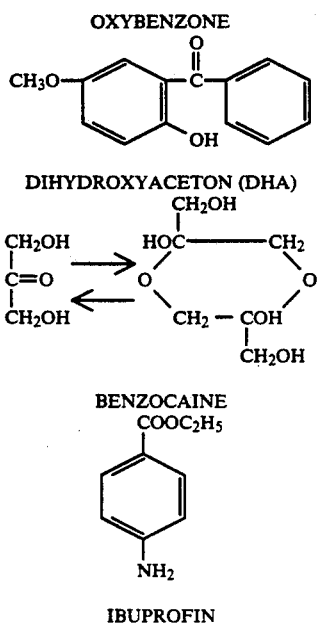

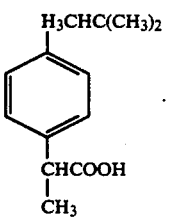

EXAMPLE 9

Solubility: 1 GM of Ester/9 GM of Solvent

The solubility of both the commercially available esters and the esters of this invention used in these trials are as follows:

|  | ETHANOL | MINERAL OIL | VOLATILE SILICONE | PROP. GLY. | GLY. | H$_2$O |
|---|---|---|---|---|---|---|
| *Commercial Esters* | | | | | | |
| FINSOLV | | | | | | |
| TN[1] | S | S | S | I | I | I |
| P[2] | S | S | S | D | D | I |
| BOD[3] | D | S | S | I | D | I |
| SB[4] | S | S | S | I | I | I |
| EH-25[5] | S | S | S | D | I | I |
| *ESTERS OF THE INVENTION* | | | | | | |
| Glucam E-10 BENZOATES of Invention | S | I | I | S | I | Emul. |
| Glucam E-20 BENZOATES of Invention | S | I | I | S | D | Emul. |

Where s = soluble, I = Unsoluble d = dispensibility Emul = emulsion formed
[1]Finsolv TN = Cbd 12-15 Alkyl-Benzoate
[2]Finsolv P = Stearoxy-Polypropoxy-Benzoate
[3]Finsolv BOD = Octyl-Dodecyl-Benzoate
[4]Finsolv SB = Isostearyl-Benzoate
[5]Finester EH-25 = C$_{12-15}$-Octanoate.

These results demonstrate that the solubility advantages of the esters of this invention are in their improved affinity for water/propylene and glycol/glycerin. These esters produce clear systems at low concentrations of 3 to 5% with the aid of surfactants like AZI-A or MD-318C.

EXAMPLE 10

Surface Tension Measurements

Surface tension measurements of the esters of this invention versus the glucam material is as follows:

| | Surface Tension (dynes/cm) | | |
|---|---|---|---|
| | 100% | 10% sol'n | 1% Sol'n |
| EMG-10 Benzoate | 39.8 | 40.9 | 42.9 |
| Glucam E-10 Polyol | 43.4 | 43.6 | 49.3 |
| EMG-20 Benzoate | 42.1 | 37.3 | 41.2 |
| Glucam E-20 Polyol | 48.0 | 42.7 | 45.9 |

The lower surface tensions of the benzoate esters at each concentration indicate that these materials will spread better on the skin. This ability is of value in skin care and cosmetic products to help give better distribution of the product on the skin, to give a more uniform film and to aid in controlling the film thickness (thinner being more aesthetically pleasing).

Having an ester in a composition present that lowers the surface tension of the solution can contribute to foam production in a positive way.

A lower surface tension is useful in formulating soaps and boosting foam volume.

EXAMPLE 11

Skin Care Compositions of this Invention

A series of compositions were prepared, such as:

(1) a liquid soap (Table 1)
(2) a self-tanning lotion (Table 2)
(3) a day skin beauty lotion (Table 3)
(4) an urban protection day cream (Table 4)
(5) a hydrophilic ointment base (Table 5)
(6) a water-in-oil lotion with vitamins (Table 6)
(7) an antiperspirant stick (Table 7).

TABLE 1

| LIQUID SOAP (81-128D) | |
|---|---|
| Component | % by Weight |
| Distilled Water | 55.8 |
| Sodium C14-16 Olefin Sulfonate | 20.0 |
| Sodium Cocoye Methyl Taurate | 10.0 |
| Lauramide DEA | 4.0 |
| Quaternium-75 | 2.0 |
| Glycol Stearate | 2.0 |
| Glycerin | 2.0 |
| EMG-20 - BENZOATE of Invention | 2.0 |
| DMDM Hydantoin | 0.2 |
| Sodium Chloride | 2.0. |

TABLE 2

| SELF TANNING LOTION (81-122C) | |
|---|---|
| Component | % by Weight |
| PEG-40 Stearate | 8.0 |
| Cetyl Alcohol | 1.0 |
| EMG-20 - BENZOATE of Invention | 6.0 |
| Tocopheryl Acetate | 3.0 |
| Distilled Water | 73.3 |
| Glycerin | 3.2 |
| Dihydroxyacetone | 5.0 |
| Diazolidinyl Urea, Propylene Glycol Methylparaben, Propylparaben. | 0.5 |

TABLE 3

| DRY SKIN BEAUTY LOTION | | | | |
|---|---|---|---|---|
| | % by Weight | | | |
| Component | 81-112A | 81-139A | 81-139B | 81-139C |
| Propylene Glycol Monostearate | 3.0 | 3.0 | 3.0 | 3.0 |
| Cetyl Alcohol | 1.0 | 1.0 | 1.0 | 1.0 |
| Stearic Acid | 2.5 | 2.5 | 2.5 | 2.5 |
| Isopropyl Myristate | 1.0 | 1.0 | 1.0 | — |
| C12-15 Alkyl Benzoate | — | — | — | 1.0 |
| EMG-10-BENZOATE of Invention | — | 5.0 | — | — |

TABLE 3-continued
DRY SKIN BEAUTY LOTION

| Component | % by Weight | | | |
|---|---|---|---|---|
| | 81-112A | 81-139A | 81-139B | 81-139C |
| EMG-20-BENZOATE of Invention | 5.0 | — | 5.0 | 5.0 |
| Triethanolamine, 99% | 0.8 | 0.8 | 0.8 | 0.8 |
| Distilled Water | 86.7 | 86.4 | 86.4 | 86.4 |
| Diazolidinyl Urea, Propylene Glycol, Methylparaben, Propylaparaben. | — | 0.3 | 0.3 | 0.3 |

TABLE 4
URBAN PROTEOTION DAY CREAM (81-129B)

| Component | % by Weight |
|---|---|
| Water | 65.0 |
| Carbomer 1342 (2%) | 15.0 |
| Glycerin | 2.0 |
| Cetearyl Alcohol & Cetaereth-20 | 1.0 |
| EMG-20-BENZOATE of Invention | 2.0 |
| Dimethicone | 0.5 |
| Diazolidinyl Urea, Propylene Glycol, Methylparaben, Propylparaben | 1.0 |
| Water/Lecithin/Superoxide Dismutase | 10.0 |
| Water/Lecithin Tocopheryl Acetate | 3.0 |
| Aminomethyl Propanol | 0.2 |
| Selenium Protein | 0.3. |

TABLE 5

A hydrophilic ointment base can be prepared—i.e., an oil-in-water emulsion. The base is typical of those used in topical pharmaceutical ointments and can include components as follows. The resultant product is a smooth spreading ointment base, which when applied to the skin should provide a pleasant emolliency, yet without a greasy feel.

HYDROPHILIC OINTMENT BASE (81-151B)

| Component | % by Weight |
|---|---|
| Stearyl Alcohol | 10.0 |
| Glyceryl Stearate | 3.0 |
| EMG-20-BENZOATE of Invention | 9.0 |
| Propyl Paraben | 0.15 |
| Distilled Water | 72.70 |
| Propylene Glycol | 4.0 |
| PEG-100 Stearate | 1.0 |
| Methyl Paraben | 0.15. |

TABLE 6
WATER-IN OIL LOTION WITH VITAMINS (81-130E)

| Component | % by Weight |
|---|---|
| Cyclomethicone/Dimethicone Copolyol | 9.5 |
| Cyclomethicone | 6.0 |
| Tocopheryl Acetate | 2.0 |
| Pareth 25-3 | 0.5 |
| EMG-20-BENZOATE of Invention | 5.0 |
| Propylparaben | 0.15 |
| Distilled Water | 72.7 |
| Sodium Chloride | 2.0 |
| Methyl Paraben | 0.15 |
| Panthenol | 2.0. |

TABLE 7
ANTIPERSPIRANT STICK

| Component | % by Weight | |
|---|---|---|
| | 81-20D | 81-20E |
| Cyclomethicone | 43.5 | 43.5 |

TABLE 7-continued
ANTIPERSPIRANT STICK

| Component | % by Weight | |
|---|---|---|
| | 81-20D | 81-20E |
| Stearyl Alcohol | 23.0 | 23.0 |
| EMG-10-BENZOATE of Invention | 5.0 | — |
| EMG-20-BENZOATE of Invention | — | 5.0 |
| Hydrogenated Castor Oil | 2.0 | 2.0 |
| Steareth-20 | 1.0 | 1.0 |
| Silica | 0.5 | 0.5 |
| Aluminum Chlorhydrate | 25.0 | 25.0. |

What is claimed is:

1. A benzoic acid ester of an ethoxylated methyl glucoside of the formula:

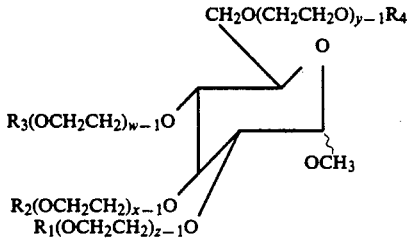

wherein $R_1$, $R_2$, $R_3$ and $R_4$ are each

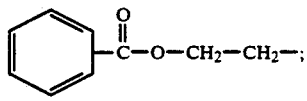

and wherein $W+X+Y+Z$ is an average of about 10–20.

2. A benzoic acid ester of a propoxylated methyl glucoside of the formula:

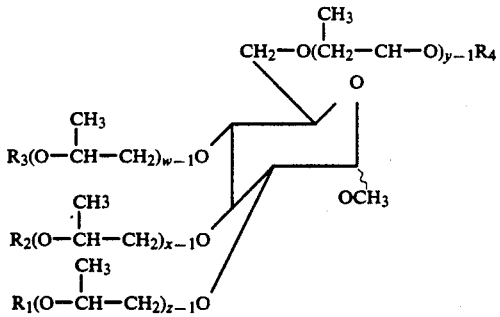

wherein $R_1$, $R_2$, $R_3$ and $R_4$ are each

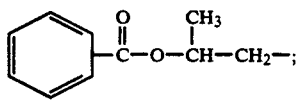

and and wherein $W+X+Y+Z$ is an average of 10 to about 20.

* * * * *